United States Patent [19]

Nicolai et al.

[11] 4,362,167
[45] Dec. 7, 1982

[54] DIAGNOSTIC MEASURING INSTRUMENT

[76] Inventors: Donald R. Nicolai, Box 415, Monticello, Minn. 55362; Oliver D. Hanson, 2255 Viking Blvd., NW., Cedar, Minn. 55011

[21] Appl. No.: 231,928

[22] Filed: Feb. 6, 1981

[51] Int. Cl.³ .............................................. A61B 5/10
[52] U.S. Cl. .................................. 128/778; 33/143 C
[58] Field of Search ............... 128/774, 775, 777, 778, 128/780, 781; 33/143 C

[56] References Cited

U.S. PATENT DOCUMENTS

| | | | |
|---|---|---|---|
| 2,301,574 | 11/1942 | Oot et al. | 33/143 C |
| 4,204,548 | 5/1980 | Kurz | 128/778 |
| 4,294,264 | 10/1981 | Fischell et al. | 128/778 |

Primary Examiner—Kyle L. Howell
Assistant Examiner—Daniel P. Burke
Attorney, Agent, or Firm—Orrin M. Haugen; Thomas J. Nikolai

[57] ABSTRACT

A diagnostic instrument comprising a pair of contact tips and control apparatus movable in a first direction to cause movement of the tips in opposite directions along a line normal to the first direction.

5 Claims, 10 Drawing Figures

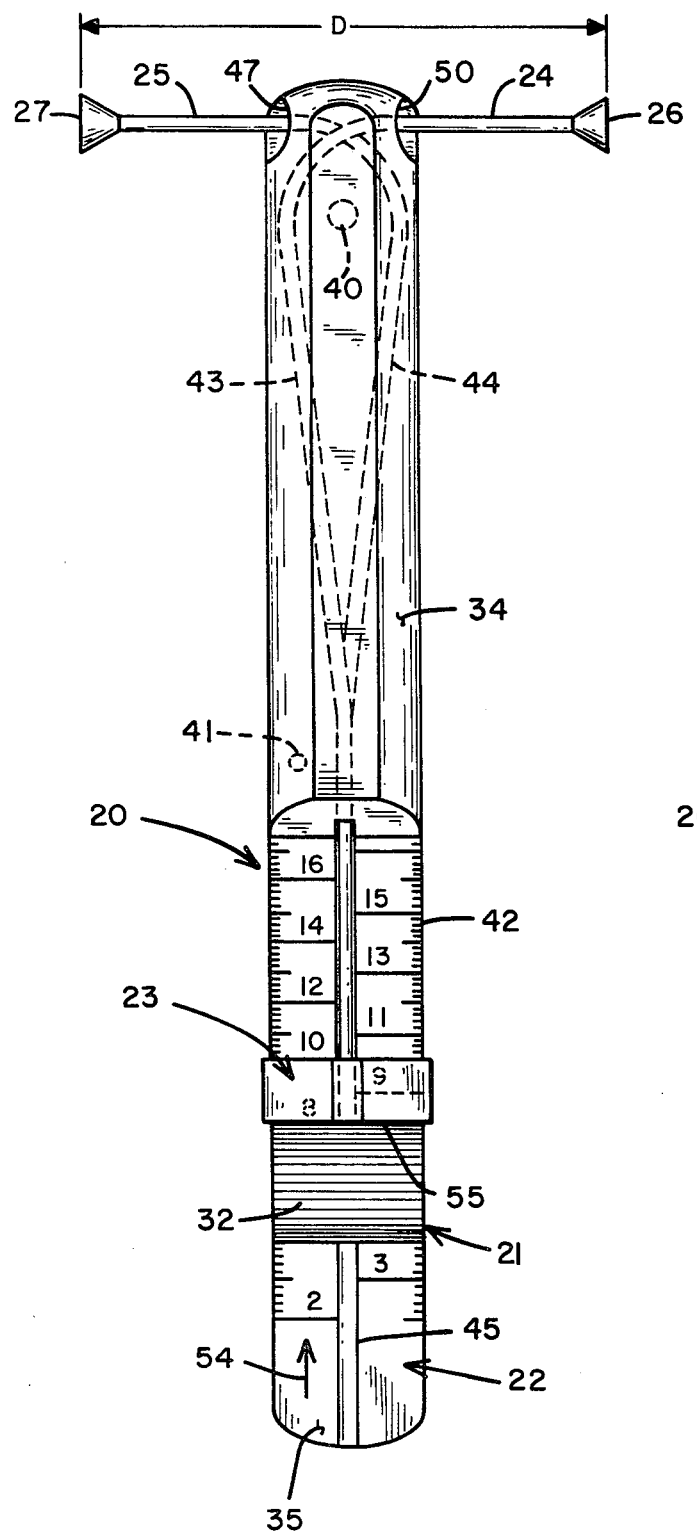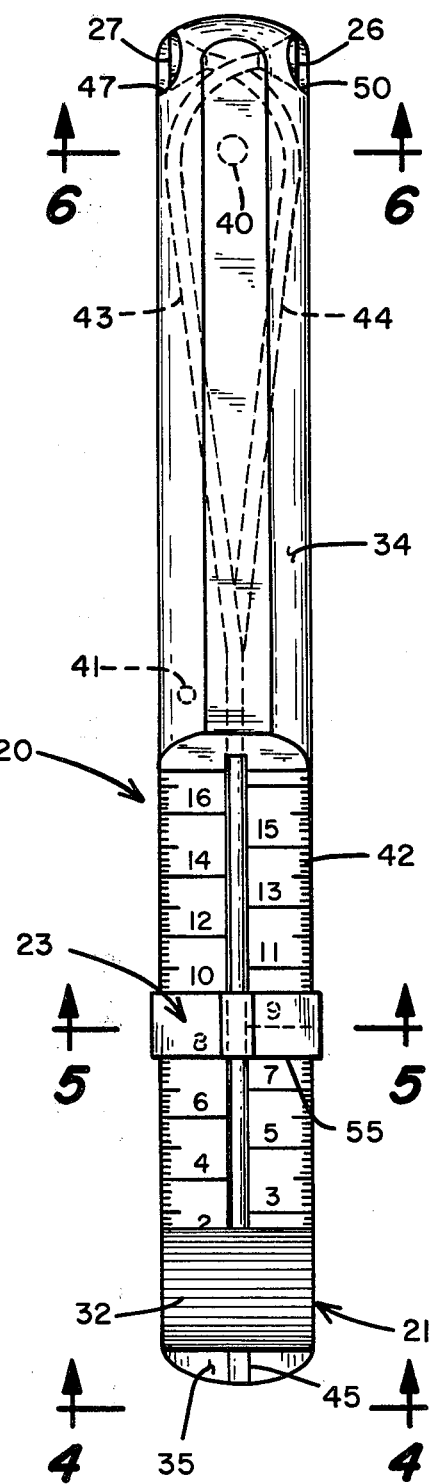
Fig. 1
Fig. 2

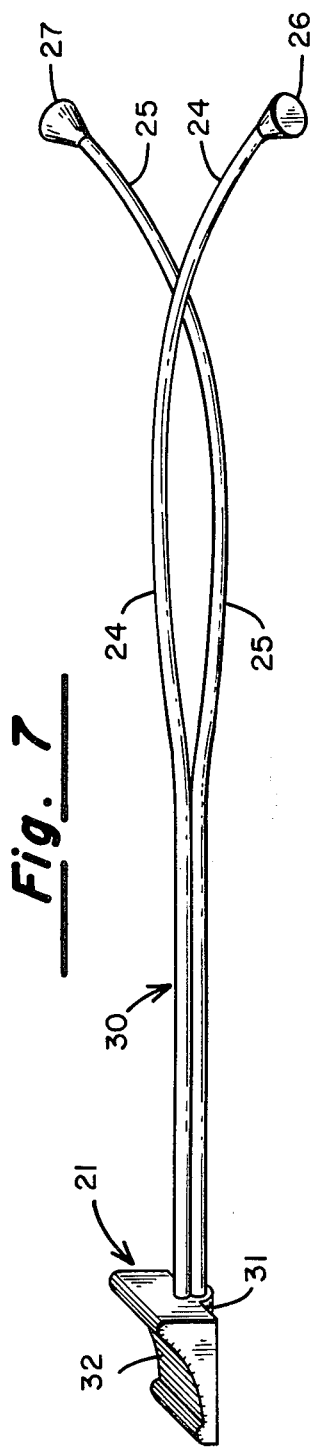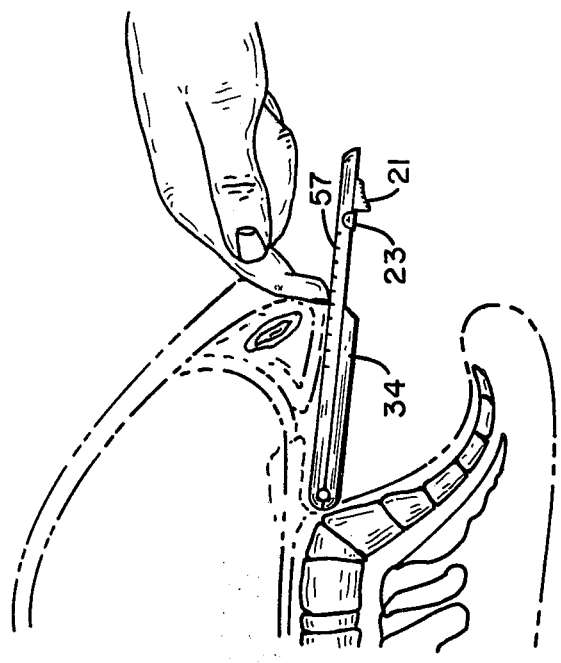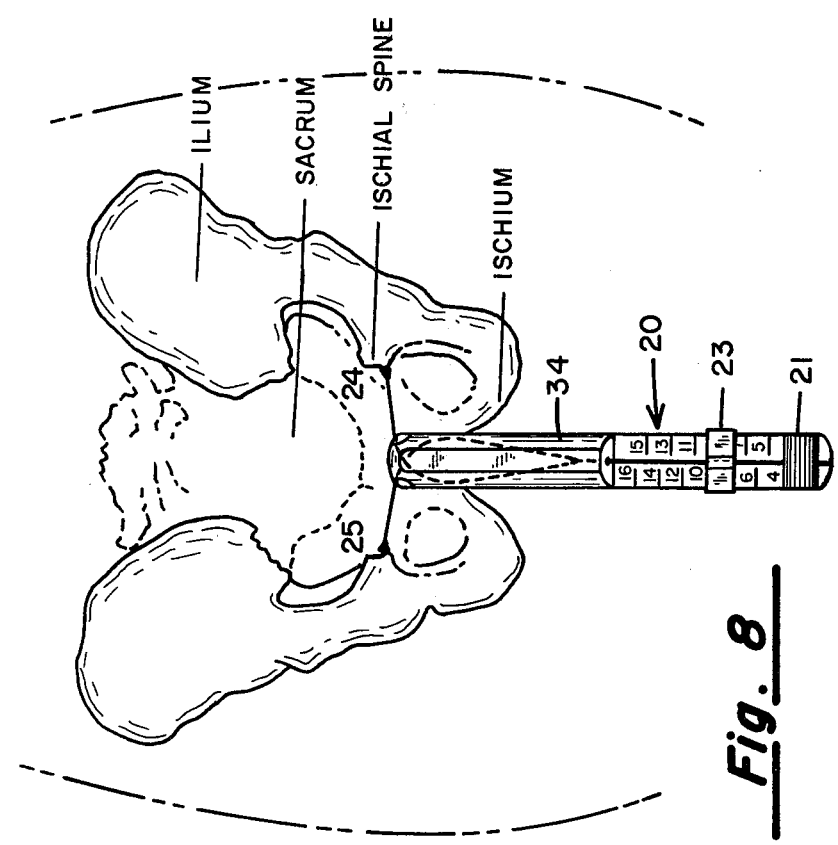

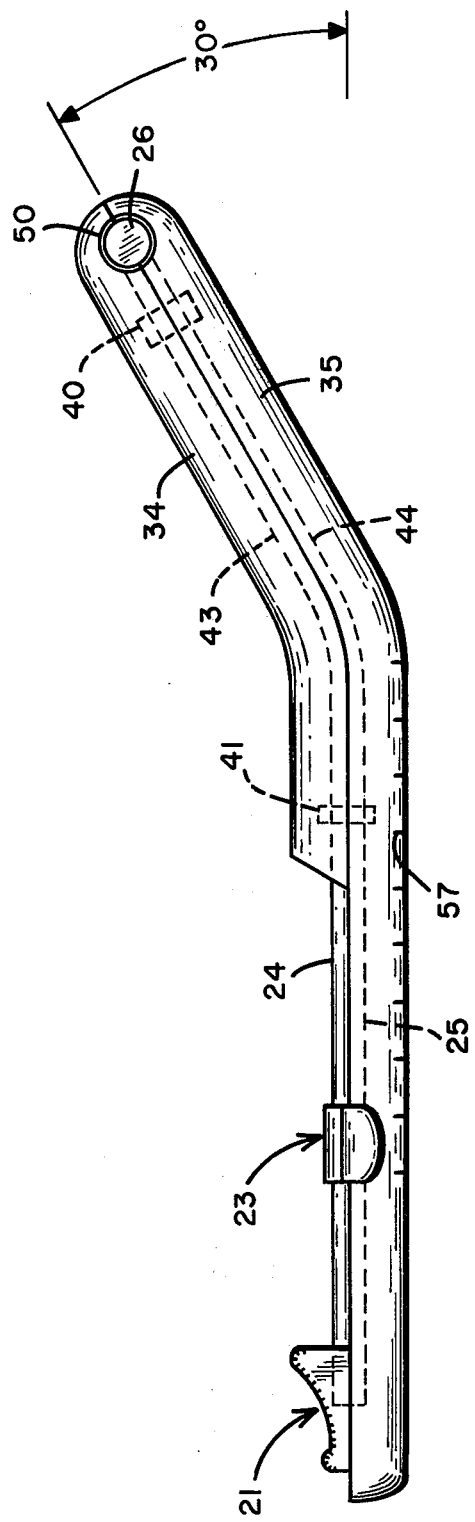

DIAGNOSTIC MEASURING INSTRUMENT

TECHNICAL FIELD

This invention relates to the field of medical instruments, and particularly to an intra-vaginal ischial probe for use in pelvimetric analysis to determine the internal transverse inter-ischial spinous diameter of a pregnant women as an indication of whether vaginal or cesarean delivery of the patient is to be elected.

BACKGROUND OF THE INVENTION

The basic determination which a gynecologist must make afresh with each new patient is whether a pregnancy has a favorable prognosis for vaginal delivery, or whether cesarean delivery will probably be required, as is the case for patients having contracted pelves.

The adult pelvis is composed of four bones defining an opening through which the normal delivery of a fetus takes place. If the passageway is not of adequate dimensions, delivery by cesarean section is indicated. One of the most significant dimensions in this connection is the distance between the ischial spines. Heretofore this distance has been determined by palpating the patient, or with the aid of X-ray pelvimetry. The former process relies heavily on the skill of the physician, and the latter requires the use of equipment and personnel not always available, and has the danger of radiological damage to the mother or fetus, in addition to its high cost.

BRIEF DESCRIPTION OF THE INVENTION

The present invention comprises an inexpensive, safe, simple instrument by which the internal transverse inter-ischial spinous diameter of the patient may be determined by the gynecologist without a supplemental radiologist. It may be used as an adjunct to direct palpation, and gives an immediate and accurate measurement of the distance in question, with minimum expense to the physician and no expense or radiological hazard to the patient. The measurement may be obtained at any time during pregnancy prior to fetus descent.

Various advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there are illustrated and described certain preferred embodiments of the invention.

BRIEF DESCRIPTION OF THE DRAWINGS

In the drawings, in which like reference numerals identify like elements throughout the several views;

FIG. 1 is a plan view of the instrument with probe tips extended as in making a measurement;

FIG. 2 is a similar view of the instrument with the probe tips retracted as after taking a measurement;

FIG. 7 shows in perspective a probe assembly according to the invention;

FIG. 8 schematically shows the instrument in use measuring the internal transverse inter-ischial spinous diameter of a patient;

FIG. 9 schematically shows the instrument in use measuring the diagonal conjugate of a patient; and FIG. 10 is a view like FIG. 3 showing a modification of the invention.

DESCRIPTION OF THE PREFERRED EMBODIMENT

Figure 3:
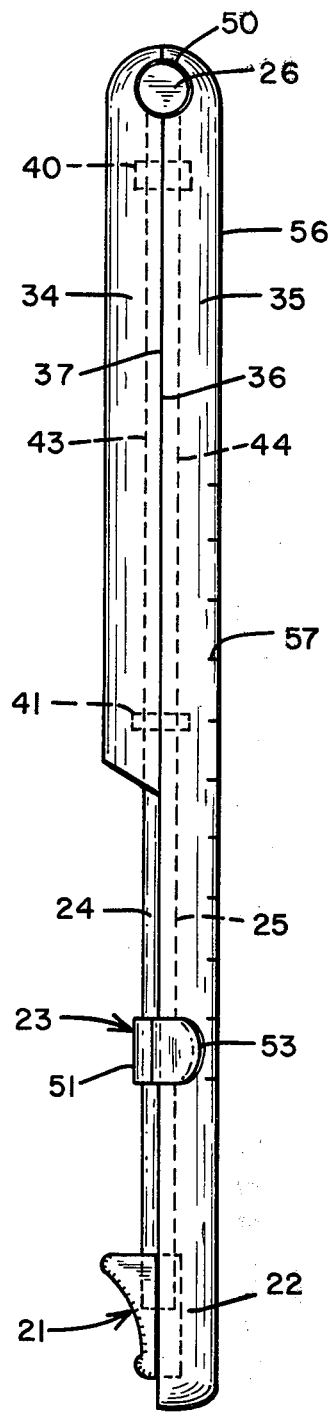
FIG. 3 is a side view of the instrument.
Figure 4:
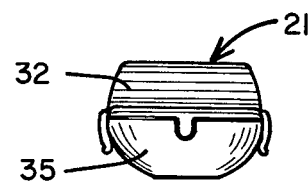
FIG. 4 is an end view of the instrument seen from the line 4—4 of FIG. 2.
Figure 5:
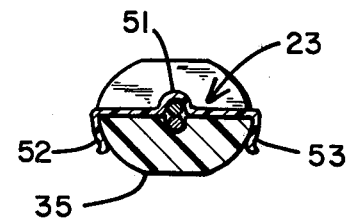
FIGS. 5 and 6 are transverse sectional views taken along the lines 5—5 and 6—6, respectively, of FIG. 2.
Figure 6:
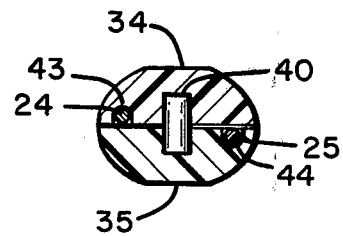

Referring now to the drawings, a diagnostic instrument 20 according to the invention is shown to comprise a probe assembly 21, a guide assembly 22, and a marker slider 23. Probe assembly 21 comprises a pair of elongated filaments 24 and 25 having probe tips 26 and 27 at distal ends thereof. The other ends of the filaments are connected to extend in the same direction from a control member 30 having a guidance tongue 31 aligned with the direction of the filaments and a thumb control knob 32.

Guide assembly 22 comprises a shorter upper portion 34 and a longer lower portion 35 joined along flat surfaces 36 and 37, their relative position being ensured by a pair of pegs 40 and 41. Portion 35 extends beyond portion 34 and its flat surface 37 is provided with a scale 42 having linear graduations extending transversely thereof. A curved channel 43 for filament 24 is formed in portion 34, and a similar channel 44 for filament 25 is formed in portion 33, and is continuous with a longitudinal groove 45 for receiving and guiding tongue 31 of member 40. A pair of cavities 47 and 50 large enough to receive probe tips 27 and 26 are formed in portions 34 and 35, extending laterally into the distal ends thereof.

Marker slider 23 has a central arch 51 to pass filament 24 and a pair of resilient lateral fingers 52 and 53 which frictionally engage the sides of portion 35. The slide may be of transparent material suitably domed to act as a lens for reading scale 42, or may be provided with separate optical means for performing this function, if desired.

Filaments 24 and 25 are flexible in the sense that they are capable of being bent, without damage, at comparatively sharp radii, but are nevertheless sufficiently rigid that force applied to member 30 in the "inward" direction of arrow 54 in FIG. 1 causes movement of the filaments through their channels. The channels are configured so that when the control member is moved, probe tips 26 and 27 extend laterally from or retract into cavities 50 and 47, the lateral distance D between the tips increasing with displacement of the control member inward. The graduations on scale 42 are correlated with this distance D.

It will be evident that when member 32 is moved inwardly slider 23 is also displaced along scale 42. On the other hand, when member 32 is moved in the other direction the slide remains in its then position, and an edge 55 of the slider accurately indicates the maximum displacement of member 30 and hence the maximum value of distance D.

FIG. 8 suggests how the instrument performs its function. With tips 26 and 27 retracted and with the probe lying in the palm of the physician's hand and aligned with his extended index finger, the distal end of the instrument is inserted into the patient's vagina and properly positioned, by internal palpation with his index finger, so that as the tips are extended they contact the ischial spines of the patient. Movement of the tips is accomplished by use of thumb knob 32, and is accompanied by movement of slider 23. When the measurement has been taken, the tips are retracted by reverse movement of thumb knob 32 to facilitate instrument removal, but slider 23 remains in its advanced position, so that after the instrument has been withdrawn the value of distance D can be read, on scale 42, at edge 55 of the slider.

As an added feature of convenience, the outer surface 56 of portion 35 is provided with a further linear scale 57 graduated in linear distance from the distal end of the instrument, to assist the physician in measuring the patient's diagonal conjugate, as suggested schematically in FIG. 9.

For certain anatomical configurations, the instrument may preferably take the form shown in FIG. 10. Here portions 34 and 35 are bent so that apposed surfaces 36 and 37 define a dihedral angle having an apex to which the line of distance D is parallel. Some pelves have anatomical idiosyncrasies for which this modified structure is preferable.

In the case of both embodiments of FIGS. 3 and 10, the portions 34 and 35 are held together, during use, by friction pins 40 and 41. To facilitate cleaning and sterilization, however, the parts 34 and 35 may be separated to expose the interior channel portions and to free the filaments 24 and 25.

From the foregoing, it will be evident that we have invented a diagnostic instrument for use in measuring the internal transverse inter-ischial spinous diameter and the diagonal conjugate of a patient. For the first measurement, the instrument comprises a pair of probe tips and means operative to extend and retract the tips transversely with respect to a guide assembly, and for indicating on a properly calibrated scale the maximum distance between the tips. A second scale facilitates the second measurement, and a modified form of the invention is shown for use in cases of anatomical idiosyncrasies.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

We claim:

1. A diagnostic instrument comprising, in combination:
   (a) a probe assembly including a pair of elongated flexible filaments, a tongued control member to which first ends of said filaments are secured so that they extend therefrom in the same direction, and a pair of cupped tips at the other ends of said filaments; and
   (b) a guide assembly having first and second apposed portions, one of said portions being extended and receiving the tongue of said control member and guiding it in a first, longitudinal direction, said portions being separately channeled to pass said filaments respectively so that they change directions by generally 90° to extend laterally from one end of said guide assembly in opposite directions, whereby linear movement of said control member results in opposite motions of said tips along a line transverse to said guide assembly.

2. An instrument according to claim 1 in which the extension of said one of said portions includes a flat surface having graduations extending in said first direction and correlated with the position of said control members as a function of the transverse distance between said tips of said filaments.

3. An instrument according to claim 1 and further including a marker sliding on and frictionally engaging the extension of said one of said portions for movement with respect to said graduations by movement of said control member in a first direction which increases said transverse distance between said tips.

4. An instrument according to claim 3 in which said filaments pass under said marker before reaching the channels in said portions of said guide assembly.

5. An instrument accordingly to claim 1 in which said portions are formed with a bend, making a predetermined dihedral angle with said flat surface having an apex, to which the line joining said tips remain substantially parallel.

* * * * *